United States Patent
Matsui (10) Patent No.: US 7,488,404 B2
(45) Date of Patent: Feb. 10, 2009

(54) PROCESS FOR HYDROGENATING CARBON DIOXIDE, TREATING APPARATUS, AND BASIC MATERIAL FOR HYDROGENATION

(76) Inventor: Masayoshi Matsui, 26-30, Zenpukuzi 2-chome, Suginami-ku, Tokyo (JP) 167-0041

(*) Notice: Subject to any disclaimer, the term of this patent is extended or adjusted under 35 U.S.C. 154(b) by 752 days.

(21) Appl. No.: 11/155,653

(22) Filed: Jun. 20, 2005

(65) Prior Publication Data
US 2005/0263391 A1 Dec. 1, 2005

Related U.S. Application Data

(62) Division of application No. 10/493,064, filed as application No. PCT/JP02/11456 on Nov. 1, 2002, now Pat. No. 7,064,150.

(30) Foreign Application Priority Data

Nov. 6, 2001 (JP) ............................ 2001-376464
Feb. 28, 2002 (JP) ............................ 2002-101899

(51) Int. Cl.
*C25D 17/00* (2006.01)
(52) U.S. Cl. ...................... 204/206; 204/210; 205/137; 205/138; 205/141
(58) Field of Classification Search ................ 204/206, 204/210; 205/137, 138, 141
See application file for complete search history.

(56) References Cited

U.S. PATENT DOCUMENTS 3,660,262 A * 5/1972 Spiller ........................ 204/499
6,068,755 A * 5/2000 Matsuda et al. ............. 205/333

FOREIGN PATENT DOCUMENTS

| EP | 539 244 | 4/1993 |
|---|---|---|
| JP | 3-200734 | 9/1991 |
| JP | 3-258737 | 11/1991 |
| JP | 4-72376 | 3/1992 |
| JP | 5-18359 | 3/1993 |
| JP | 6-184023 | 7/1994 |

OTHER PUBLICATIONS

"Investigation on Technology for $CO_2$ Fixation and Effective Utilization/3/New Energy and Industrial Technology Development Organization," pp. 159-167, Mar. 1993 (with partial English translation).
T. Inui, pp. 79-89, "Carbon Dioxide-Chemical/Biochemical/Environment-Catalytic Hydrogenation," 1994 (with partial English translation).

* cited by examiner

*Primary Examiner*—Nam X Nguyen
*Assistant Examiner*—Luan V Van
(74) *Attorney, Agent, or Firm*—Oblon, Spivak, McClelland, Maier & Neustadt, P.C.

(57) ABSTRACT

A process for hydrogenating carbon dioxide to generate methanol. In the process, a strip of copper base plate is transported by the groups of rotating drive rollers to deposit porous metallic zinc on the copper base plate. Hydrogen is generated from the porous metallic zinc upon electrochemical reactions in the inner space sealed with the above groups of rollers. Simultaneously, zinc oxide and copper oxide catalysts are formed on the porous metallic zinc. Carbon dioxide is introduced into the sealed inner space under high-temperature and high-pressure to generate methanol by hydrogenation.

8 Claims, 4 Drawing Sheets

PROCESS FOR HYDROGENATING CARBON DIOXIDE, TREATING APPARATUS, AND BASIC MATERIAL FOR HYDROGENATION

This Application is a Divisional application of Ser. No. 10/493,064 filed on Apr. 30, 2004 which is a national stage of PCT/JP02/11456 filed Nov. 1, 2002.

TECHNICAL FIELD

The present invention relates to a process for hydrogenating carbon dioxide using a synthetic catalyst mainly composed of a mixed oxide of zinc and copper, thereby generating methanol as a main product, and an apparatus therefor.

BACKGROUND ART

At present, global warming is considered an urgent issue and one of the most important tasks for humanity to deal with, as it could endanger the existence of humans. Carbon dioxide, a large quantity of which has been accumulated in the world due to the use of fossil fuels, accounts for much of the global warming phenomenon. Further, the rate of carbon dioxide emission has recently increased exponentially, and numerous intensive studies have been conducted all over the world to develop techniques for dealing with this issue.

Examples of conventional techniques for hydrogenating carbon dioxide in order to fix carbon dioxide include photoelectrochemical techniques utilizing natural energy, such as sunlight, and biochemical techniques utilizing microorganisms. Disadvantageously, the efficiency of these techniques is low, and the rate of processing is much lower than that of carbon dioxide emission. The reduction of carbon dioxide with the use of a catalyst was the only conversion technique having a sufficient rate of processing. This procedure, however, requires a specific reaction vessel in which hydrogen and carbon dioxide can be simultaneously subjected to catalytic reactions in the presence of an adequate catalyst at sufficiently high temperature and high pressure. Furthermore, a relatively low-temperature synthetic catalyst, for example, a methanol synthetic catalyst that causes reactions at 250° C. to 300° C., mainly composed of a mixed oxide of zinc and copper, must be first prepared, accommodated in a reaction vessel, subjected to reactions, and replaced with another catalyst at any time. Accordingly, this procedure must be intermittently carried out, which prevents the processing of emitted carbon dioxide in large quantities. There exits many literatures concerning the hydrogenation of carbon dioxide, although conventional techniques suffer from serious drawbacks as described below.

The chemical formula of hydrogenating carbon dioxide is shown as below.

[Chemical Formula 1]

(The symbol "-" denotes heat generation. The same applies hereinafter.)

According to this chemical formula, the conversion rate at chemical equilibrium cannot be exceeded due to thermodynamic restrictions. It is highly insufficient to conduct the above reaction using a main catalyst of zinc or copper oxide since the conversion rate is as low as approximately 40% under reaction conditions of approximately 200° C. to 250° C. at 50 atm to 100 atm, and many substances remain unreacted. In this case, therefore, unreacted substances must be recycled by being separated after the reaction and then subjected to reactions again, or a selective permeable membrane must be used to separate the product from unreacted gas. Thus, conventional techniques are not yet sufficient due to the necessity for considerably complicated equipment, as well as the existence of technical and practical difficulties.

DISCLOSURE OF THE INVENTION

The present invention considerably differs from conventional processing techniques as mentioned above in ideas. An object of the present invention is to provide a process for hydrogenating carbon dioxide that is capable of processing a large quantity of carbon dioxide to generate a large quantity of methanol as a main product, thereby engaging with the rapidly spreading issue of global warming. It is another object of the present invention to yield significant economic effects through the use of the thus obtained methanol. Such methanol has potential to be an important fuel for the future, and can be used as an alternative to fossil fuels, an agricultural material for growing plants, and for other basic materials. Thereby, use of the aforementioned process can be developed as a social enterprise.

In order to attain the above objects of the present invention, a porous layer was employed as a basic material. This porous layer is composed of: a long band like strip of copper base plate 1; both of porous metallic zinc layers 2 and 3, or the layer 2, which have been moistened with electrolytes, immobilized on both sides of the copper base plate 1 by electrolysis; and a catalyst comprising a main catalyst of zinc oxide, copper, and copper oxide obtained through oxidation as described below and other additional substances for hydrogenating carbon dioxide on both or half of the porous metallic zinc layers 2 and 3.

The aforementioned electrolysis is carried out by adopting the aforementioned copper base plate 1 as a cathode in an electrolyte prepared by adding zinc oxide as a main component to a caustic alkali solution. Thus, porous metallic zinc layers with very large surface areas and high levels of activity are electrodeposited on both sides of the base plate (see JP Laid-open Patent Publication (Kokai) No. 4-72376), and oxygen is generated from an anode. This electrolysis reaction is represented by the following chemical formula.

[Chemical Formula 2]

The electrolytes deposited on the surfaces of the electrolyzed base plate are removed, and the porous metallic zinc layers are moistened in order to prepare both or half of the layers as a catalyst. For this purpose, metallic zinc should be oxidized to prepare zinc oxide, and a copper compound, such as copper oxide, an additional substance as a promoter, such as aluminum, chromium oxide, lanthanum, or an oxide thereof, noble metals, such as platinum, palladium, silver, or nickel, transition metals, such as rhodium or copper, and a rare earth element, such as lanthanum, or oxides thereof should be incorporated in the porous zinc layers solely or in combinations of two or more. Aluminum, copper, chromium, lanthanum, and oxides thereof are particularly useful. These additional substances can be added and mixed by any means without particular limitation.

Both or half of the porous layers that have been processed as mentioned above and moistened with electrolytes are sealed in the inner space formed between two rows of many drive rollers that are in close contact with each other as described in Examples below. A metal having a low hydrogen overvoltage, such as nickel, iron, or platinum, is brought into contact with the porous metallic zinc layer in this sealed space to form an electrical circuit. Thus, hydrogen is actively generated via electrochemical reactions from the surface that is in contact with the aforementioned metal having a low hydrogen overvoltage. At the same time, the porous metallic zinc is oxidized to form an oxide layer. The spaces inside and outside of the oxide layer are filled with hydrogen gas, and the atmosphere therein becomes a high pressure. The aforementioned metal having a low hydrogen overvoltage may be in the form of a plate, a strip, or particles. This condition is represented by the chemical formula below.

$$Zn+H_2O \rightarrow ZnO+H_2\uparrow$$ [Chemical Formula 3]

Hydrogen gas can be generated through flowing external current electrification instead of the occurrence of an electrical short circuit due to the internal contact as mentioned above.

The conditions of the oxide layer are brought to a state of high-temperature, high-pressure, and dehydration by, for example, heating the sealed spaces inside and outside of the aforementioned layer of the catalyst, such as zinc or copper oxide with an electric heater. Alternatively, a porous zinc layer 3, which is located on the opposite side of the porous layer 2, is moistened with an electrolyte. It is rapidly oxidized by the introduction of oxygen or air, heat is generated, and the temperature is raised. This generated heat is immediately conducted to the porous layer 2 on the opposite side through the copper base plate 1, which is situated between the two layers so as to separate one layer from the other. Thus, the conditions thereof can be brought to a state of high-temperature, high-pressure, and dehydration. This reaction is represented by the chemical formula below.

$$2Zn+O_2 \rightarrow 2ZnO-83.2 \text{ kcal/mol}$$ [Chemical Formula 4]

A reference should be made to JP Examined Patent Publication (Kokoku) No. 5-18359 concerning this exothermic reaction. The temperature of the generated heat was found to become as high as at least 700° C. based on the research conducted after the publication of this patent application. The generated heat is immediately conducted to the porous layer on the opposite side, and the conditions thereof are brought to a state of high-temperature, high-pressure, and dehydration.

As mentioned above, hydrogen gas is generated at high temperature and high pressure. When carbon dioxide is injected in the presence of an oxide of zinc or copper and a variety of additional substances as promoters as mentioned above, hydrogen reacts rapidly with carbon dioxide, and methanol is generated as a main product in a manner as shown in Chemical Formula 1. The generated methanol gas is liquefied upon collection and cooling thereof, and methanol can be recovered as a main product. The aforementioned process for hydrogenating carbon dioxide has been already put to practical use (see, for example, *Gendai Kagaku* (*Contemporary Chemistry*), Extra Issue 25, "*Nisanka Tanso* (*Carbon Dioxide*)," p. 79, Inoue, Izui, Tanaka (ed.), Tokyo Kagaku Dojin Co., Ltd., Nov. 16, 1994). As means for solving the object, the present invention satisfies all the requirements for hydrogenation in terms of a catalyst, a starting gas, temperature, and pressure naturally. Thus, a large quantity of carbon dioxide can be rapidly processed without any special equipment. In addition, the present invention is characterized in that methanol can be mass-produced as a useful main product, i.e., can kill two birds with one stone (Japanese proverb). The present invention is not limited to the use of carbon dioxide described above. Carbon monoxide or a mixed gas composed of carbon dioxide and carbon monoxide can also be used. Also, the product generated according to the present invention is not limited to methanol. Methane, formaldehyde, ethanol, and other substances can also be generated.

The process for mass-producing methanol with very high efficiency of the present invention is described below.

Figure 1:
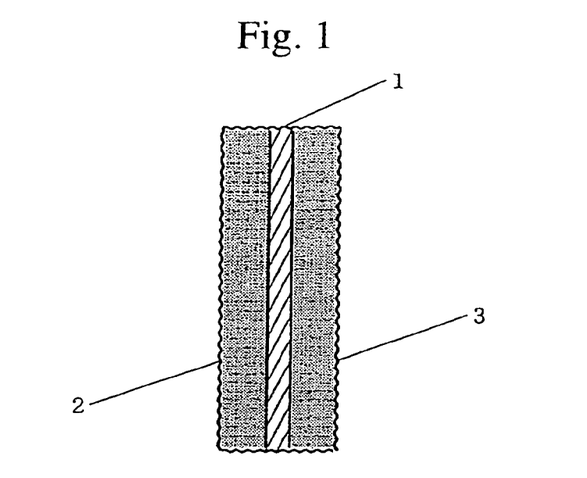
FIG. 1 is an enlarged diagram showing a cross-section of a copper base plate comprising porous metallic zinc layers on both of its sides.
Figure 5:
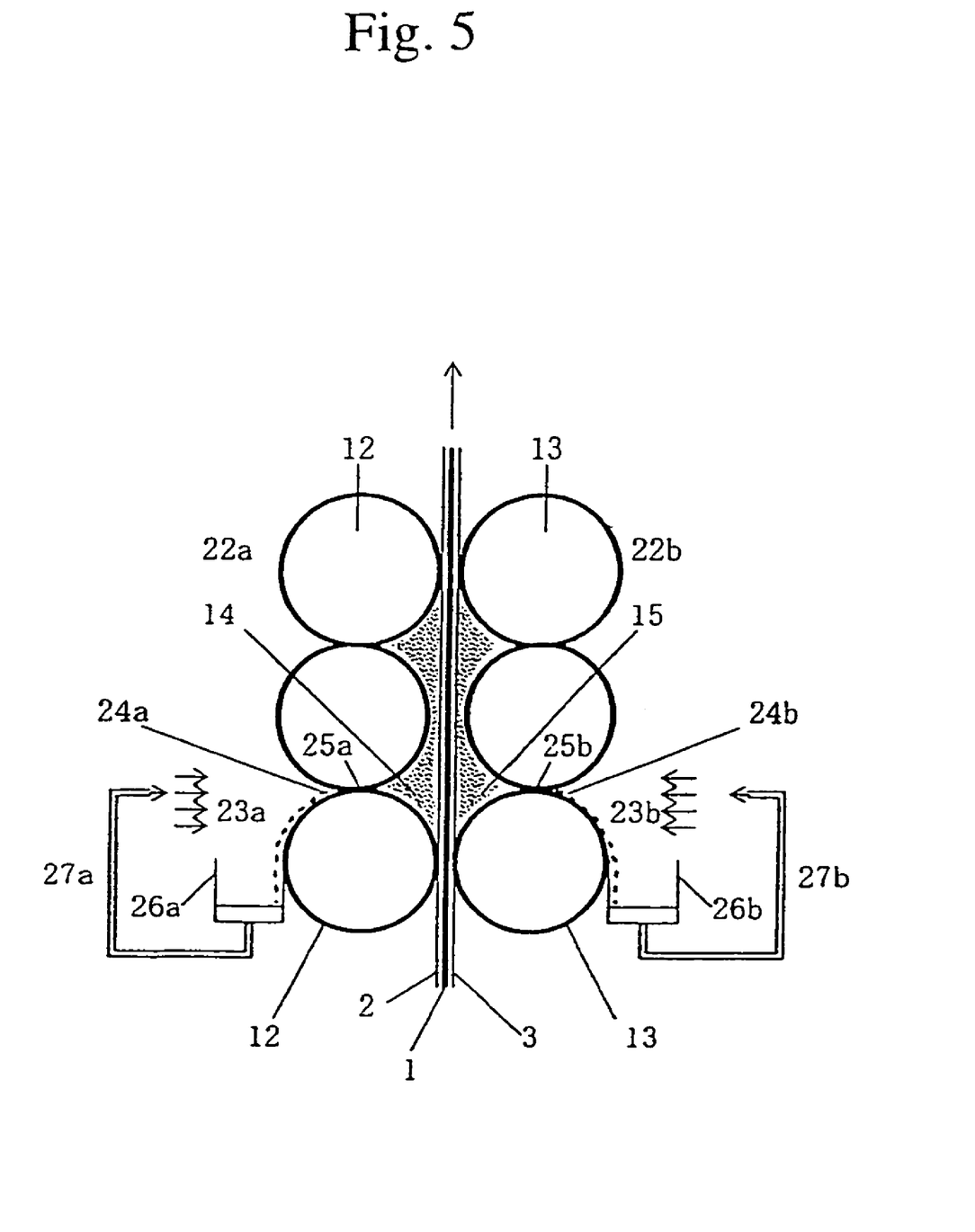
FIG. 5 is an enlarged elevational view of the apparatus described in Example 3.

The present invention is intended to yield a large quantity of methanol as well as possess a high capacity for processing carbon dioxide. Mainly, water is rapidly and continuously discharged to the outside of the reaction system at the same time as the generation of the product shown in the right-hand side of Chemical Formula 1. The low conversion rate of approximately 40% due to thermodynamic restrictions is maximized to attain the above object. More specifically, when the porous body used in the present invention as shown in FIG. 1 migrates forward between groups 12 and 13 of drive rollers which have elastic surfaces so as to move in conjunction with the adjacent rollers that are in close contact with each other as shown in FIG. 5, the inner spaces 14 and 15 (FIG. 5) formed within the groups of rollers become sealed, have a high temperature, and have a high pressure because of the containment of carbon dioxide and hydrogen gas. Thus, methanol and water vapor are generated by the reaction represented by Chemical Formula 1. In such a state, cold air or coolants 23a and 23b are supplied from the outer spaces 22a and 22b, which are located outside of the aforementioned inner spaces and have conditions of room temperature and normal pressure, toward the circumscribed surfaces 24a and 24b formed along the groups of rollers. Thus, the aforementioned surfaces 24a and 24b of the groups 12 and 13 of rollers, respectively, are located contiguously with the circumferences of the tangent planes with which the groups of rollers are in close contact. These spaces are cooled even though the thermal conductivity of rollers is low. Thus, as the water vapor in the inner spaces or the water vapor containing the generated methanol reaches the dew point, thin liquid layers 25a and 25b are formed on the tangent planes of the aforementioned rotating drive rollers, and the water-sealed state can be maintained. It should be noted that the surfaces of the above groups of rollers must have hydrophilic properties such as those of a titanium oxide coating in order to form the liquid layers. Also, it is advantageous to provide fine irregularities, streak patterns, and the like on the surfaces so as to impart water-retentive properties without interfering with the sealed state.

If the reaction represented by Chemical Formula 1 yields a conversion rate of approximately 40% at 250° C. and 50 atm, the water vapor in the inner space is condensed to reach at its dew point, based on the partial pressure when it is cooled to approximately 160° C. or lower. The aforementioned thin liquid layers 25a and 25b are thus obtained. Subsequently, water obtained by cooling of the inner spaces passes through liquid layers 25a and 25b, and afterwards is diffused to the circumscribed surfaces 24a and 24b in accordance with the rotating direction of the group of rollers, and is cooled to room temperature of the outer spaces 22a and 22b or lower with the aid of coolants 23a and 23b. Thus, water is completely discharged. Discharged water is recovered in receivers 26a and 26b provided at the outside of the groups 12 and 13 of rollers at their lower positions. Only a very small amount of methanol may be contained in the condensed water at 160° C.

Discharged water contained in the receivers 26a and 26b may be circulated via ducts 27a and 27b for water recovery and recycled and reused as coolants 23a and 23b. Alternatively, cold air may be adopted, as well as the aforementioned coolants.

Accordingly, water shown in the right-hand side of Chemical Formula 1 is the only substance that is mainly and continuously discharged to the outside of the reaction system and then separated. Thus, the conversion rate quickly reaches approximately 90% or higher. This should be understood based on the predictions described in the following technology report. If calculated under assumption that, more specifically, even if 90% of the water generated in the reaction represented by Chemical Formula 1 employing a membrane reactor could be extracted, the calculated correlation between the reaction pressure and the rate of equilibrium conversion at each temperature exhibited large values of approximately 90% or higher at any temperature. It is that above results could be very different from a case where water was not extracted (see "$CO_2$ *koteika, yuukou riyou gijutsu ni kansuru chousa* (*Investigation concerning the effective techniques of immobilizing $CO_2$ and effective use thereof*)", 3, *Shin enerugi, sangyo gijutu* (*New energy, industrial techniques*), p. 159, 1993, 3). Such a high rate of conversion predicates that a critical object of the present invention was almost attained and that a variety of distinctive features as mentioned below were obtained.

BEST MODES FOR CARRYING OUT THE INVENTION

The present invention is described in more detail with reference to the attached diagrams.

EXAMPLE 1

Figure 2:
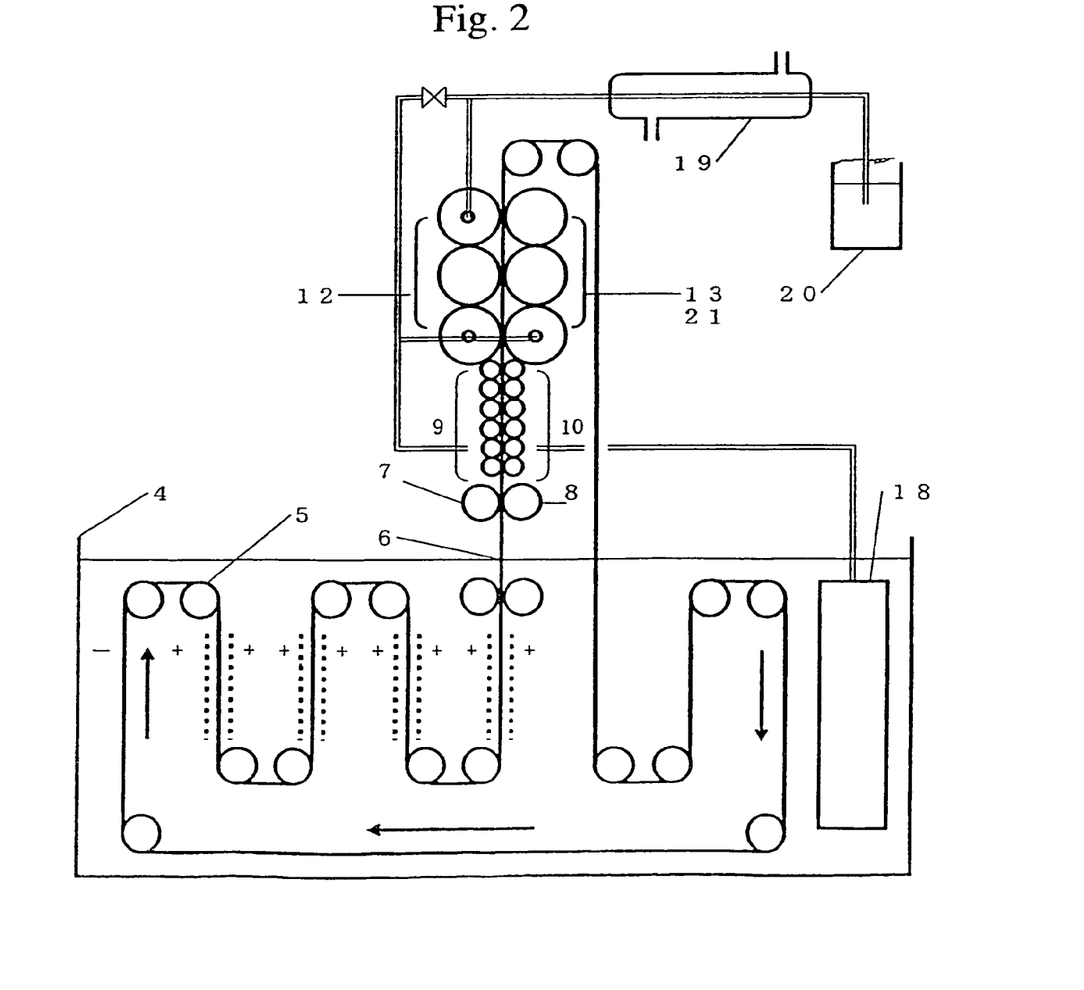
FIG. 2 schematically shows the entire process for hydrogenating carbon dioxide.

As shown in FIG. 2, a strip of thin copper base plate 1 (thickness: 0.1 mm) is electrolyzed while being guided in the upward and downward directions among plural drive rollers 5 in an electrolyte accommodated in an electrolytic bath 4, and it migrates forward. An electrolyte to be used is an emulsion comprising 50 g of zinc oxide powder per liter of a solution comprising 100 g of caustic potash per liter thereof. The base plate 1 that migrates within an electrolyte while employing anode of insoluble plates, such as zinc plates, immobilized on both of its sides. The base plate 1 continuously migrates forward while being electrolyzed cathodically at 5 $A/dm^2$ by adopting the insoluble plates as anodes and the base plate 1 as a cathode. Active porous metallic zinc layers are deposited and immobilized on both sides of the base plate 1 during this electrolysis. The amount of zinc to be deposited is adjusted by regulating the current density of the electrolysis on both sides of the base plate 1. Also, as a whole, the duration of electrolysis is regulated.

Over a period of 40 minutes, porous metallic zinc layers are deposited and immobilized on both sides of the electrolyzed base plate 1 up to the level of the electrolyte surface 6. The base plate then migrates upward and exceeds the electrolyte surface. The base plate is then pressed with drive rollers 7 and 8 to a porosity of approximately 90%. Thus, excess amounts of electrolyte contained in the porous metallic zinc layers 2 and 3 are removed, and the porous layers further migrate in the upward direction while maintaining their moistened states. By being pressed with rollers, porous metallic zinc layers are firmly immobilized on both sides of the base plate 1 by means of pressure bonding, and both sides of the base plate are hard in stratified and moistened with electrolytes. In this case, the total of the thickness of the base plate 1, that of the porous layer 2, and that of the porous layer 3 was approximately 0.8 mm.

When copper oxide powders are sprinkled on the porous metallic zinc layers 2 and 3 provided on both sides of the base plate 1 before the base plate enters between rollers 7 and 8, one portion of the porous layers are reduced to metallic copper by metallic zinc. However, other portions form porous metallic zinc layers comprising copper oxide. In such a case, the aforementioned additional substances, such as alumina, chromium oxide, or other substances that can be used as subcatalyst for zinc oxide or copper oxide catalysts, may be incorporated therein.

Figure 3A:
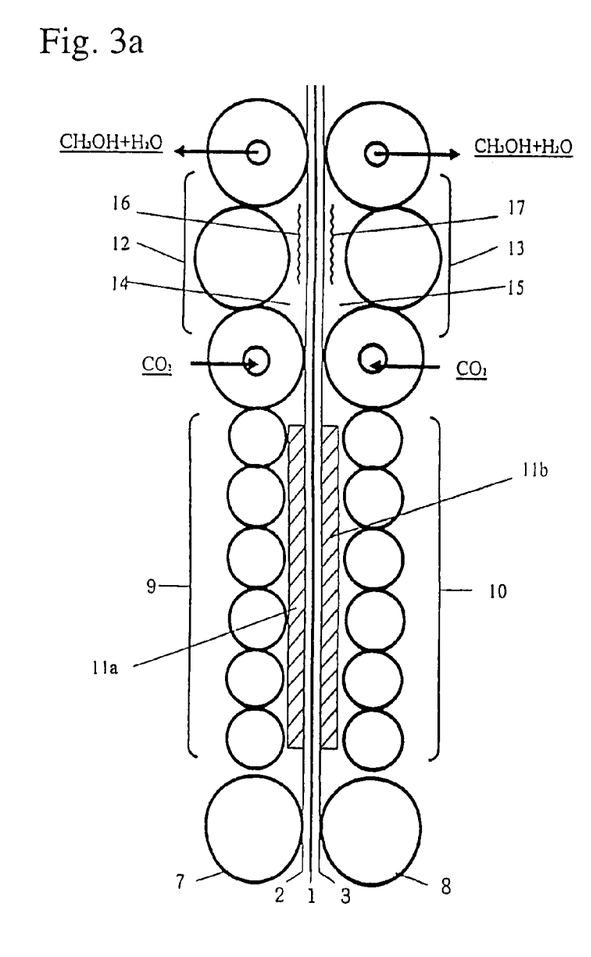
FIG. 3a is an enlarged elevational view of the apparatus described in Example 1.
Figure 3B:
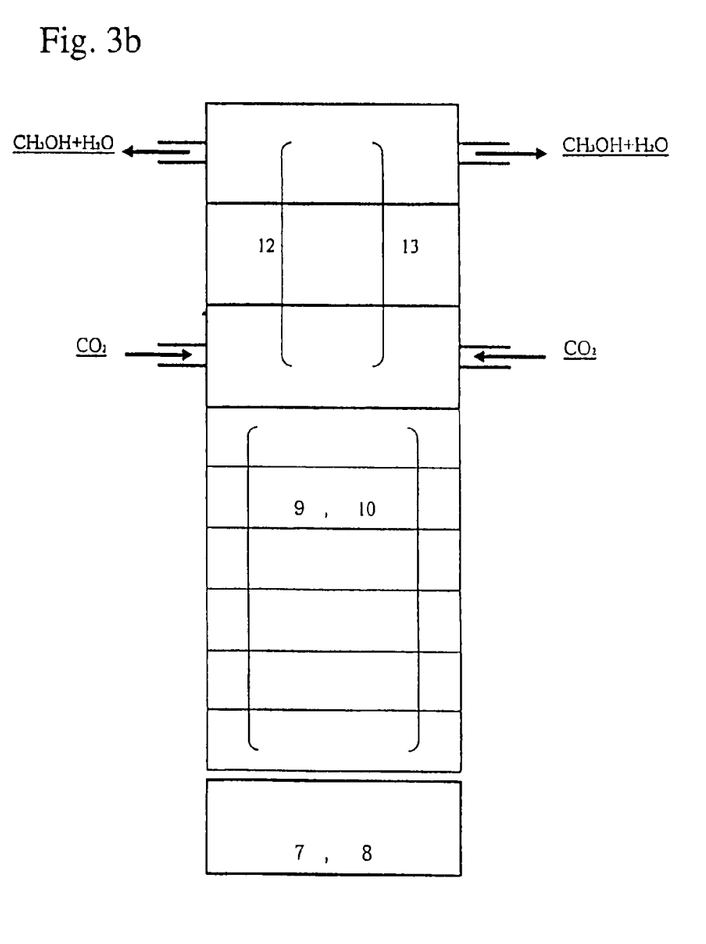
FIG. 3b is an enlarged plane view thereof.

Thus, the base plate 1 migrates upward to be sandwiched between plural rotating drive rollers. FIG. 3a and FIG. 3b are detailed and enlarged diagrams showing this procedure. The drawing is roughly divided to show the groups 9 and 10 of drive rollers for generation of hydrogen as shown in Chemical Formula 3 and the groups 12 and 13 of drive rollers for reaction as shown in Chemical Formula 1.

The surface of each roller of the groups 9, 10, 12, and 13 of plural drive rollers is uniformly elastic, and adjacent rollers are in close contact with each other. Thus, the inner spaces formed by the groups of rollers can be sealed. Further, the base plate 1, which passes between the rollers, completely separates the porous layer 2 from the porous layer 3 provided on the opposite side of the base plate 1. Accordingly, the porous layers 2 and 3 on both sides of the base plate can be independently sealed. Since adjacent rollers in a group of rollers are rotated while remaining in close contact with each other, every other roller inversely rotates, and friction may be caused between a roller and the porous zinc layer that passes between the rollers. In order to avoid this inconvenience, the diameters of the inversely-rotating rollers are made somewhat smaller than those of other rollers, and thus, the porous zinc layers do not come into contact with the inversely-rotating rollers. The roller diameters can be regulated by any means without particular limitation.

Both ends of each roller are covered with covers in order to seal the inner spaces.

The inner spaces formed within the group of plural rollers move upward while maintaining their sealed conditions. Both porous layers 2 and 3, which have been moistened with electrolytes, are brought into contact with thin nickel plates 11a and 11b, which are immobilized so as not to move in conjunction with the groups 9 and 10 of plural drive rollers, so as to be electrolyzed forming an electrical circuit or introducing through external circuit. At the same time, active hydrogen is generated from the nickel plate immediately after the reaction in a manner as shown in Chemical Formula 3, and zinc in the porous layer is converted to zinc oxide. Generated hydrogen is gradually accumulated, and the pressure thereof increases as it moves upward in the inner space. In order to generate methanol as a main product and water by allowing hydrogen to react with carbon dioxide as shown in Chemical Formula 1, inlets for carbon dioxide and outlets for the reaction products are separately provided at the center portions of some drive rollers 12 and 13. Carbon dioxide is injected into the inner spaces 14 and 15 through the aforementioned inlets in order to allow these spaces to be filled with a mixture of high-pressure carbon dioxide and hydrogen. At the same time, the inner spaces 14 and 15 are heated with electric heaters 16 and 17, and conditions of zinc oxide, copper oxide, and the like of the porous layers 2 and 3 are brought to a state of dehydration, high-temperature, and high-pressure. It is advantageous to provide plural drive rollers in order to achieve pressure as high as 50 atm to 100 atm. A total of 6 rollers are provided in the case of the apparatus shown in the drawing. Carbon dioxide is vaporized with the aid of the Joule's heat generated upon electrolysis from dry ice accommodated in the pressure-tight vessel 18 in the electrolyte in the electrolytic bath. This can prevent the temperature of the electrolyte from rising and can vaporize carbon dioxide, i.e., killed two birds with one stone (Japanese proverb). In the inner space with pressure of approximately 50 kg/cm$^2$, the partial pressure of hydrogen is approximately 37.5 kg/cm$^2$, and that of carbon dioxide is approximately 12.5 kg/cm$^2$, according to Chemical Formula 1. Carbon dioxide sources are not limited thereto. Specifically, a large quantity of carbon dioxide is emitted in industrial activities, particularly for the automobile industry, and a large quantity of highly concentrated carbon dioxide is emitted from thermal power plants, factories, waste incineration plants, and large-sized automobiles. Utilization of such waste gas is highly beneficial.

Although the use of carbon dioxide was solely mentioned above, gas of carbon oxide compounds, such as carbon monoxide or a mixed gas composed of carbon monoxide and carbon dioxide, may also be used.

Thus, a porous layer having a catalyst layer for hydrogenating carbon dioxide is formed in the inner space, hydrogen and carbon dioxide are mixed with each other at this location, and the entire inner space becomes heated to a temperature of 250° C. to 300° C. and pressurized to between 50 atm and 100 atm. Accordingly, conditions required for hydrogenating carbon dioxide, thereby generating methanol as a main product, are all satisfied spontaneously, and reactions as shown in Chemical Formula 1 immediately take place. Generated methanol as a main product and water vapor are discharged through the outlets for reaction products provided at the center portions of some of the groups 12 and 13 of rollers, cooled with the aid of a cooler 19, and recovered in the receiver 20. For example, approximately 8 g of hydrogen is needed relative to 60 g of carbon dioxide. The amount of zinc required therefor is approximately 270 g, and the quantity of electricity is approximately 220 Ah. The theoretical yield of methanol is approximately 40 g, and the rate of conversion in such a case is approximately 40%. Unreacted hydrogen and carbon dioxide can be injected through the lower positions of the drive rollers 12 and 13 and then subjected to reactions again.

The copper base plate 1 that had passed between the groups 12 and 13 of rollers comprises oxide layers of zinc, copper, or the like adhering to both of its sides. As shown in FIG. 2, the base plate 1 is returned again to the electrolyte in the electrolytic bath by being guided by the drive rollers. Because of its electrolyte-soluble properties, the oxide layer is separated and reprocessed as an electrolyte. Thus, the copper base plate 1 can be repeatedly used.

Use of the process and the apparatus described in this example in combination with those described in Example 3 below results in, for example, a significantly enhanced rate of conversion as shown in Chemical Formula 1, a large methanol yield, and a significantly increased rate of consumption of carbon dioxide and hydrogen.

EXAMPLE 2

The description made in Example 1, line 10 on page 8 to line 3 on page 9, is also applicable in this example.

As shown in FIG. 2, when copper oxide powders are sprinkled on the porous metallic zinc layer 2 provided on one side of the base plate 1 before the base plate enters to roller 7, portions of the porous layer are reduced to metallic copper with the aid of metallic zinc. However, other portions form a porous metallic zinc layer comprising copper oxide. In such a case, the aforementioned additional substances that can be used as subcatalyst for zinc oxide or copper oxide catalysts may be incorporated therein.

Figure 4A:
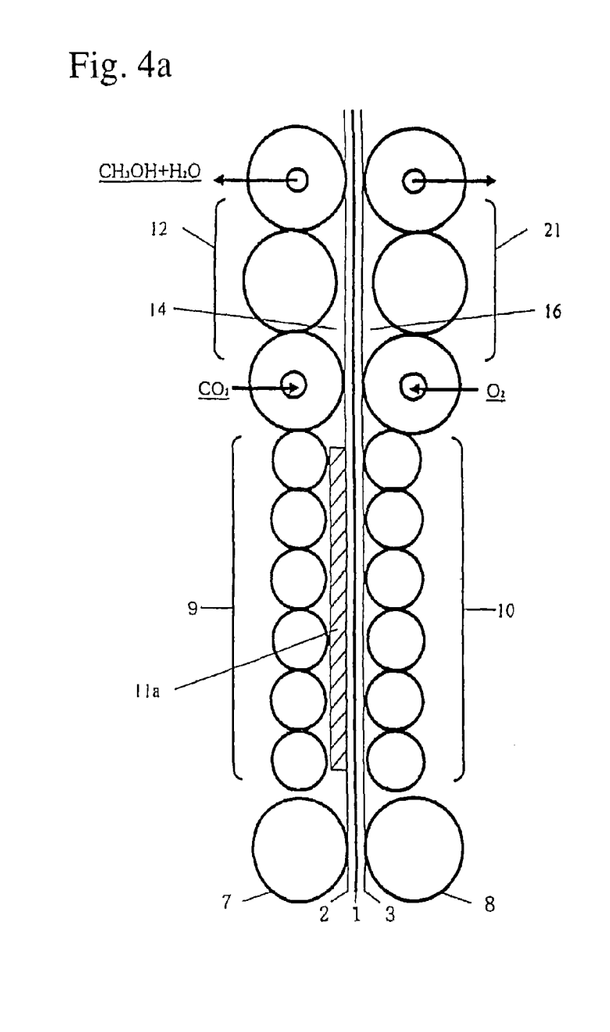
FIG. 4a is an enlarged elevational view of the apparatus described in Example 2.

Thus, the base plate 1 migrates upward to be sandwiched between plural rotating drive rollers. FIG. 4a (an elevational view) and FIG. 4b (a plane view) are detailed and enlarged diagrams showing this procedure. The drawings are roughly divided to show the group 9 of drive rollers for generating hydrogen as shown in Chemical Formula 3, the group 10 of drive rollers in contact with the porous zinc layer 3, the group 12 of drive rollers for the reaction shown in Chemical Formula 1, and the group 21 of drive rollers for the reaction shown in Chemical Formula 4. The surface of each roller of the groups 9, 10, 12, and 21 of plural drive rollers is uniformly elastic, and adjacent rollers are in close contact with each other. Thus, the inner spaces formed by the groups of rollers can be sealed. Furthermore, the base plate 1, which passes between the rollers, completely separates the porous layer 2 from the porous layer 3 provided on the opposite side of the base plate 1. Accordingly, the porous layers 2 and 3 on both sides of the base plate can be independently sealed. Since adjacent rollers in a group of rollers are rotated while remaining in close contact with each other, every other roller inversely rotates, and friction may be caused between a roller and the porous zinc layer that passes between the rollers. In order to avoid this inconvenience, the diameters of the inversely-rotating rollers are made somewhat smaller than those of other rollers, and thus, the porous zinc layer does not come into contact with the inversely-rotating rollers. The roller diameters can be regulated by any means without particular limitation. The groups of rollers that can be kept sealed at high pressure and high temperature are as described in Example 1.

Figure 4B:
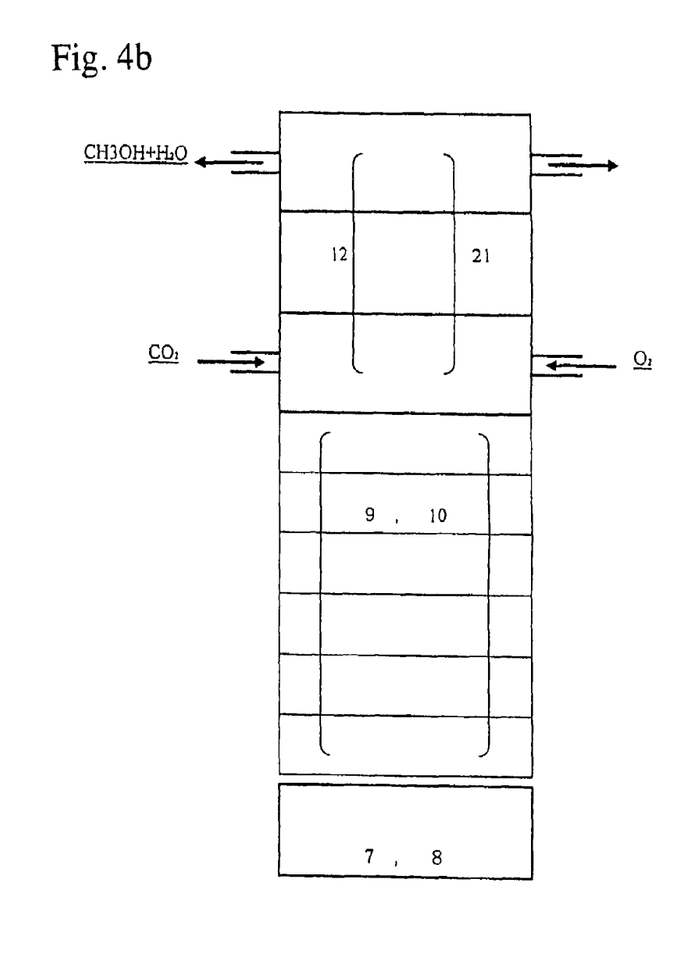
FIG. 4b is an enlarged plane view thereof.

The inner spaces formed within the groups of plural rollers move upward while maintaining their sealed conditions. The porous layer 2, which has been moistened with an electrolyte, is brought into contact with a thin nickel plate 11a, which is immobilized so as not to move in conjunction with the group 9 of plural drive rollers, so as to be electrolyzed forming an electrical circuit or introducing through external circuit. At the same time, active hydrogen is generated from the nickel plate immediately after the reaction in the manner shown in Chemical Formula 3, and zinc in the porous layer is converted to zinc oxide. The aforementioned nickel may be in the form of a plate, a strip, or particles. Since the spaces around the porous oxide layer are sealed as mentioned above, hydrogen is gradually accumulated, and the pressure thereof increases as it moves upward in the inner space. Thus, the inner space 14 formed between the group 12 of drive rollers for generating methanol as a main product is filled with hydrogen. Inlets for carbon dioxide and outlets for the reaction products are separately provided at the center portions of some groups of rollers.

In contrast, an inlet and an outlet for oxygen or air are provided at the center portion of the group 21 of drive rollers for reaction located on the side of the porous zinc layer 3, which is the opposite side of the porous layer 2. The porous zinc layer 3 is moistened with an electrolyte. When oxygen or air is introduced into the inner space 15 through the inlet, the porous zinc layer 3 is rapidly oxidized, becoming exothermics, and the temperature is raised as shown in Chemical Formula 4. This generated heat is immediately conducted to the porous layer 2 through the copper base plate 1, which is situated between the porous layers 2 and 3 to separate one layer from the other. Thus, the porous layer 2 also comes to have a state of high-temperature, high-pressure, and dehydration. In introduction of oxygen as mentioned above, oxygen generated through the reaction represented by Chemical Formula 2 may be collected and introduced. When the dehydrated condition is attained, carbon dioxide is injected through the inlet simultaneously therewith. Thus, a mixed gas composed of hydrogen and carbon dioxide is obtained. Thus, all the conditions required for hydrogenating carbon dioxide, i.e., formation of the porous layer 2 having a catalyst layer for hydrogenating carbon dioxide, such as a layer of zinc oxide, copper oxide, or alumina, and a mixed gas composed of carbon dioxide and hydrogen having a high temperature of between 250° C. and 300° C. and a high pressure of between 50 atm and 100 atm, are satisfied inevitably. The reactions represented by Chemical Formula 1 immediately take place as with the case in Example 1, and methanol as a main product and water are generated. This reaction product is discharged through center portions of some groups of rollers, cooled with the aid of a cooler 19, and recovered in the receiver 20. Unreacted hydrogen and carbon dioxide can be injected through the lower center position of the drive roller 12 and then subjected to reactions again.

The copper base plate that had passed between the groups 12 and 21 of rollers comprises oxide layers of zinc, copper, or the like adhering to both of its sides. As shown in FIG. 2, the base plate is returned again to the electrolyte in the electrolytic bath by being guided by the drive rollers, and the oxide layer is separated and reprocessed as an electrolyte. Thus, the copper base plate 1 can be repeatedly used.

Use of the process and the apparatus described in this example in combination with those described in Example 4 below results in, for example, a significantly enhanced rate of conversion in the reaction represented by Chemical Formula 1, a large methanol yield, and a significantly increased rate of consumption of carbon dioxide and hydrogen.

EXAMPLE 3

The description made in Example 1, line 10 on page 8 to line 10 on page 9, is also applicable in this example.

In this example, the base plate 1 migrates upward between plural rotating drive rollers. FIG. 5 is an enlarged diagram showing a major part of an apparatus for hydrogenating carbon dioxide, and show a process for hydrogenating carbon dioxide for additionally explaining the apparatus and the process described in Example 1 and shown in FIG. 3a and FIG. 3b. More specifically, with the utilization of the apparatus and the process for hydrogenating carbon dioxide, water can be immediately and continuously discharged to the outside of the reaction system simultaneously with the generation of the reaction product shown in the right-hand side of Chemical Formula 1, thereby enhancing the rate of conversion with low chemical equilibrium and enhancing the yield of methanol. The explanation thereof is the same as described from line 10 on page 6 to line 24 on page 7.

In the examples as mentioned above, approximately 8 g of hydrogen is needed relative to 60 g of carbon dioxide to be injected. The amount of zinc required therefor is approximately 270 g, and the quantity of electricity is 220 Ah. The theoretical yield of methanol generated is approximately 40 g, and the rate of conversion in such a case is at least 90%, i.e., at least 36 g. Thus, a critical object of the present invention was achieved. This is a result of the fact that the reaction represented by Chemical Formula 1 took place unidirectionally from the left-hand side to the right-hand side of the formula.

EXAMPLE 4

In this example, the process described in Example 3 and a part of the apparatus described in Example 3, i.e., the group 12 of rollers located on the left side of the base plate as shown in FIG. 5, were introduced into only the inner space 14 of the apparatus described in Example 2. In such a case, a heat source in the inner space where the reaction occurs is provided inevitably without any external supplementation, a large quantity of methanol is generated, and the rate of consumption of carbon dioxide and hydrogen is accelerated.

INDUSTRIAL APPLICABILITY

In conclusion, in order to deal with ever-increasing amounts of carbon dioxide accumulated, the present invention provides a novel and practically effective process for hydrogenating carbon dioxide and an apparatus therefor that can continuously fix a large quantity of carbon dioxide and recover methanol as a main product with high efficiency. Thus, the present invention yields significant economic effects, and the use of this process can be developed as a social enterprise.

The applicability of the present invention is described in detail.

1. Power sources as the primary energies supplied from solar batteries, wind power, or other sources, which are necessary in the present invention, are mainly stored in the form of electroreduced porous metallic zinc as shown in Chemical Formula 2 in order to secure power. Specifically, first, a stored power is allowed to generate by means of an electrochemical reaction immediately before the reaction at the place where hydrogen that is important for the reaction according to the present invention is required, as shown in Chemical Formula 3. At the same time, a main material, i.e., zinc oxide, of a catalyst that can be suitably used in the present invention is generated, and copper oxide and other additional substances are added thereto to prepare a catalyst. Second, heat is immediately generated to high temperature by means of the reaction represented by Chemical Formula 4, and this heat can play a major role in the hydrogenation of carbon dioxide. Third, if the aforementioned porous metallic zinc is previously stored and prepared, power sources can be continuously and stably provided so as to cope with the issue of variable power sources, such as solar batteries. In particular, the apparatus according to the present invention can be operated in spite of unstable and discontinuous power sources provided from natural energies, such as solar batteries, or temporary suspension of power sources due to discontinuous power, electric power failure or other reasons. Thus, natural energy that does not emit carbon dioxide can be effectively used. These techniques could not be expected from conventional techniques.

2. A catalyst to be used in the present invention is not necessary to be prepared in advance relative to conventional techniques. At the outset, an active porous metallic zinc layer is allowed to deposit on a copper base plate by means of electrolysis, thereby generating active zinc oxide, which is a main substance for a catalyst for hydrogenating carbon dioxide, and hydrogen applying the reaction represented by Chemical Formula 3. Copper oxide and other substances are added to zinc oxide. Thereafter, water is removed by heating to prepare an excellent catalyst, which is involved in the hydrogenation of carbon dioxide as represented by Chemical Formula 1. Thus, an active catalyst according to the present invention with a large surface area can be effectively prepared during a reaction process according to the present invention.

3. Hydrogen used in the present invention is highly active since it is generated immediately before use by means of the electrochemical reaction represented by Chemical Formula 3. A necessary amount of such active hydrogen with the necessary pressure is prepared immediately before use and immediately subjected to the generation of methanol represented by Chemical Formula 1. Thus, hydrogen can be very effective in aspects, for example, reaction rate and yield. There is feature that these effects could not be assumed from conventional techniques.

In general, whether or not the hydrogenation of carbon dioxide can prove an effective measure against global warming depends on the following two points. These are the existence of effective ways of obtaining inexpensive hydrogen and of obtaining products with high value from carbon dioxide. The present invention can prove satisfactory regarding these two points.

4. Temperature and calorific value sufficiently high for hydrogenation according to the present invention can be immediately and spontaneously obtained by means of the reaction represented by Chemical Formula 4. As is apparent from the description in the above Examples, heat required for the generation of methanol as represented by Chemical Formula 1 can be immediately conducted through the partitioning copper base plate 1 and can be effectively involved in the reaction. Although each zinc consumption of the porous metallic zinc layers 2 and 3 provided on both sides of the base plate 1 varies depending on each reaction as mentioned above, the amounts of electrodeposited zinc in the above layers 2 and 3 can be easily regulated depending on consumption.

5. In order to implement the hydrogenation according to the present invention, high temperature and high pressure are required. Implementation thereof with a conventional technique has been difficult due to the necessity of a special pressure- and heat-resistant chamber. In contrast, the object of the present invention can be relatively easily and reasonably attained, as is apparent from the Examples. Specifically, plural elastic rotating drive rollers are positioned in close contact with each other, and plural sealed spaces are separately provided. In the inner spaces formed among the rollers, hydrogen is immediately and sequentially generated by means of electrochemical reactions of porous metallic zinc as represented by Chemical Formula 3, and the internal pressure is gradually elevated to a designated level. Thus, high pressure can be easily maintained with a relatively simple and reasonable apparatus. These are effects that could not be obtained in conventional techniques. Concerning heat-resistant properties, heat can be imparted easily and selectively to desired positions since the rollers are rotating.

6. In the present invention, a novel process for hydrogenating carbon dioxide and an apparatus therefor were employed to generate methanol as a main product with a yield exceeding by 90% of the theoretical value of the reaction represented by Chemical Formula 1 due to thermodynamic restrictions. As mentioned above, a recycling method in which unreacted gas was separated and subjected to reaction again, a method in which unreacted gas was continuously separated from a reaction product using a selective permeable membrane to subject the unreacted gas to the reactions again, and other methods have been heretofore attempted. In all of these attempts, however, large-sized and complicated apparatuses were required, and effects attained therewith have not yet proven sufficient.

Thus, none of such attempts have succeeded. In contrast, the present invention considerably differs from conventional techniques in ideas. Reverse reactions are blocked and forward reactions proceed unidirectionally according to the process for hydrogenating carbon dioxide of the present invention. An apparatus for hydrogenating carbon dioxide according to the present invention is novel since a long strip of a porous body is allowed to migrate as a catalyst in the sealed inner space formed between the groups of many rotating rollers provided in continuously close contact with each other, and carbon dioxide is allowed to react with hydrogen under a high temperature and a high pressure to generate methanol as a main product and water. The tangent plane sandwiched between rollers in close contact with each other is externally cooled to allow water vapor to reach its dew point, water vapor in the inner space is liquefied, water is continuously discharged to the outside of rollers through the tangent plane, and finally, the water generated in the reaction as represented by Chemical Formula 1 is continuously discharged to the outside of the reaction system. Accordingly, the rate of reaction can be increased, the volumes of the inner spaces can be decreased, and the necessary amount of catalyst to be used can be decreased. Furthermore, high reaction efficiency can be attained in spite of low reaction temperature.

7. Generation of methanol through hydrogenation of carbon dioxide according to the present invention needs to simultaneously satisfy conditions concerning a catalyst, hydrogen, high temperature, and high heat. According to the process and the apparatus of the present invention, a main catalyst of, for example, copper oxide or zinc oxide obtained by oxidizing active porous metallic zinc is used as a basic material, reaction conditions are arranged in a correct order, and methanol as a main product can be mass-produced as a useful product with high efficiency. Such the effects could not be obtained in conventional techniques.

8. As shown in FIG. 2, the copper base plate, which had completed the process for hydrogenating carbon dioxide, returns to the electrolyte in the electrolytic bath. After the porous layers still remaining on both sides of the base plate are dissolved and removed, the base plate becomes a normal copper plate and is subjected to electrolysis again for recycling. Removed oxide is dissolved in the alkaline electrolyte and recycled as an electrolyte. Thus, the present invention is characterized in that a large quantity of carbon dioxide can be permanently and continuously processed by way of recycling.

What is claimed is:

1. An apparatus for hydrogenating carbon dioxide comprising, in the order as described below:

an electrolytic bath containing a caustic alkaline electrolyte comprising zinc oxide;

a drive roller for transporting a long strip of copper base plate in upward and downward directions in the electrolytic bath while cathodically electroreducing it therein;

drive rollers for pressing the base plate to remove excess amounts of electrolyte contained in porous layers provided on both sides of the base plate migrated beyond an electrolyte surface;

first groups of drive rollers for sealing inner spaces; and second groups of drive rollers for reactions, connected to the first groups of drive rollers, for forming inner spaces for mixing carbon dioxide with hydrogen and maintaining the high temperature and sealed conditions by heating, wherein some rollers in the second groups of drive rollers for reaction independently comprise an inlet for carbon dioxide and an outlet for reaction products, the outlet is connected to a cooler and a receiver, and a group of drive rollers is provided for transporting the base plate, which has passed through a group of drive rollers for reactions and then another group of rollers for reactions, to an electrolyte in the electrolytic bath.

2. The apparatus for hydrogenating carbon dioxide according to claim 1, wherein a pressure-tight vessel for accommodating dry ice is provided in the electrolytic bath.

3. The apparatus for hydrogenating carbon dioxide according to claim 1, wherein the groups of drive rollers comprise, in this order, the first groups of drive rollers for sealing inner spaces and the second groups of drive rollers for reaction maintaining a state of high temperature and sealing by heating, connected to the first groups, for forming inner spaces for mixing carbon dioxide and hydrogen, wherein the inner spaces formed between the drive rollers, which rotate in close contact with each other, are sealed due to the elastic surfaces of the rollers.

4. The apparatus for hydrogenating carbon dioxide according to claim 1, wherein carbon dioxide or methanol can be introduced into or discharged from both or half of the sealed inner spaces separately comprising inlets for carbon dioxide and outlets for generated methanol at the center portions of the drive rollers.

5. An apparatus for hydrogenating carbon dioxide comprising, in the order as described below:

an electrolytic bath containing a caustic alkaline electrolyte comprising zinc oxide;

a drive roller for transporting a long strip of copper base plate in upward and downward directions in the electrolytic bath while cathodically electroreducing it therein;

drive rollers for pressing the base plate to remove excess amounts of electrolyte contained in porous layers provided on both sides of the base plate migrated beyond an electrolyte surface;

first groups of drive rollers for sealing inner spaces;

a second group of drive rollers for reaction, connected to the first groups of rollers, for forming an inner space for mixing carbon dioxide with hydrogen; and a third group of drive rollers for reaction for forming an inner space for generation of heat upon contact between the porous layer and oxygen or air, wherein some rollers in the third group of rollers independently comprise an inlet and an outlet for oxygen or air at their center portions, some rollers in the second group of drive rollers independently comprise an inlet for carbon dioxide and an outlet for reaction products at their center portions, the outlet is connected to a cooler and a receiver, and a group of drive rollers for transporting the base plate, which has passed through a group of drive rollers for reactions and then another group of drive rollers for reactions, to an electrolyte in the electrolytic bath.

6. The apparatus for hydrogenating carbon dioxide according to claim 5, wherein a pressure-tight vessel for accommodating dry ice is provided in the electrolytic bath.

7. The apparatus for hydrogenating carbon dioxide according to claim 5, wherein the groups of drive rollers comprise, in this order, the first groups of drive rollers for sealing inner spaces and the second groups of drive rollers for reaction maintaining a state of high temperature and sealing by heating, connected to the first groups, for forming inner spaces for mixing carbon dioxide and hydrogen, wherein the inner spaces formed between the drive rollers, which rotate in close contact with each other, are sealed due to the elastic surfaces of the rollers.

8. The apparatus for hydrogenating carbon dioxide according to claim 5, wherein carbon dioxide or methanol can be introduced into or discharged from both or half of the sealed inner spaces separately comprising inlets for carbon dioxide and outlets for generated methanol at the center portions of the drive rollers.

* * * * *